United States Patent
Hughes et al.

(10) Patent No.: US 6,391,929 B1
(45) Date of Patent: May 21, 2002

(54) PROCESS FOR SYNTHESIZING HYDROCARBONS FROM SYNTHESIS GAS IN THE PRESENCE OF A RANEY METAL ALLOY DISPERDED IN A LIQUID PHASE

(75) Inventors: Francois Hughes, Vernaizon; Magalie Roy-Auberger, Rueil-Malmaison; Marie-Claire Marion, Vernaison, all of (FR)

(73) Assignees: Institut Francais du Petrole, Rueil Malmaison (FR); AGIP Petroli S.p.A.; ENI S.p.A., both of Rome (IT)

( * ) Notice: Subject to any disclaimer, the term of this patent is extended or adjusted under 35 U.S.C. 154(b) by 0 days.

(21) Appl. No.: 09/693,985

(22) Filed: Oct. 23, 2000

(30) Foreign Application Priority Data

Oct. 22, 1999 (FR) .............................. 99 13325

(51) Int. Cl.$^7$ .............................................. C07D 27/00
(52) U.S. Cl. ........................ 518/715; 518/700; 518/717
(58) Field of Search ................................ 518/700, 715, 518/717

(56) References Cited

U.S. PATENT DOCUMENTS 5,639,798 A * 6/1997 Wilson et al. ............... 518/714
6,087,296 A * 7/2000 Harper ........................ 502/301

FOREIGN PATENT DOCUMENTS

EP 0 087 771 A1 9/1983

OTHER PUBLICATIONS

Lun Yijun, study of raney iron catalyst for Fischer–Tropsch process in a slurry phase reactor, Proc. Annual International Coal Conf. (1997), 14th, P7/57–P7/62.*

* cited by examiner

Primary Examiner—Johann Richter
Assistant Examiner—J. Parson
(74) Attorney, Agent, or Firm—Millen, White, Zelano & Branigan, P.C.

(57) ABSTRACT

A process for synthesising hydrocarbons from synthesis gas in the presence of a catalyst essentially constituted by a Raney metal alloy dispersed in a liquid phase is described in which the catalyst comprises at least 60% by weight of at least one metal selected from metals from groups 8, 9 and 10, and optionally at least one additional element selected from alkali metals and metals from groups 4, 5, 6, 7, 8, 9, 10 and 11.

12 Claims, No Drawings

PROCESS FOR SYNTHESIZING HYDROCARBONS FROM SYNTHESIS GAS IN THE PRESENCE OF A RANEY METAL ALLOY DISPERDED IN A LIQUID PHASE

The present invention relates to a process for synthesizing hydrocarbons from a mixture comprising (CO—$CO_2$)—$H_2$ (i.e., a mixture comprising carbon monoxide and hydrogen and possibly $CO_2$, generally known as synthesis gas). This synthesis gas conversion process employs a particular catalyst, generally known as a Raney catalyst.

That type of catalyst is essentially constituted by a metal alloy comprising at least 60% by weight of at least one metal selected from metals from groups 8, 9 and 10. However, it can comprise other constituents which will be described below.

In the process of the invention, this catalyst is used in a reactor operating in the liquid phase, preferably a slurry reactor, i.e., a three-phase reactor operating with a solid catalyst in suspension in a liquid phase and in the presence of a gas phase. More preferably, the catalyst is used in a slurry bubble column type slurry reactor.

PRIOR ART

The skilled person is aware that synthesis gas can be converted into hydrocarbons in the presence of catalysts containing transition metals. Such conversion, carried out at high temperature and pressure, is known in the literature as the Fischer-Tropsch synthesis. Thus metals from groups 8, 9 and 10 of the periodic table such as iron, ruthenium, cobalt and nickel catalyze the transformation of CO—($CO_2$)—$H_2$ mixtures (i.e., a CO—$H_2$ mixture which may include $CO_2$, known as synthesis gas) to liquid and/or gaseous hydrocarbons.

Different methods have been described in the prior art, which are intended to improve the preparation of Fischer-Tropsch catalysts based on iron or cobalt supported on different supports. The most routinely used supports are alumina, silica and titanium dioxide.

Cobalt or nickel type Raney catalysts have long been used by the skilled person as catalysts for use in organic compound hydrogenation reactions.

The Raney process describes the manner of preparing a porous and active metal catalyst by first preparing a bimetallic alloy where one of the two metals can be extracted to produce a porous non soluble material which is active in catalysis (U.S. Pat. Nos. 1,628,190, 1,915,473 and 2,977,327).

A Raney catalyst is a catalyst formed by insoluble metal which is well known in Raney processes and which can typically be nickel, cobalt, copper or iron.

Raney catalysts are generally produced from an alloy of the catalytic metal under consideration (for example nickel or cobalt) with aluminium. The alloy is reduced to a powder then the aluminium is eliminated by attack using a sodium hydroxide solution, which produces a finely divided metal with a specific surface area which is generally in the range 10 to 150 $m^2/g$, more preferably in the range 10 to 100 $m^2/g$. In this form, the metal obtained (nickel or cobalt) has a large hydrogen adsorption capacity, hence its importance in catalysis.

European patent EP-A-0 648 534 describes the preparation of formed Raney metals for use in a fixed bed. Such metals can be used as an organic compound hydrogenation catalyst.

U.S. Pat. No. 4,895,994 describes forming a catalyst containing 15–50% by weight of Raney metal, a polymer and optional other additives. Such catalysts are used for hydrogenating carbon monoxide.

EP-A-0 450 861 describes the use of a slurry phase process with a catalyst based on cobalt supported on $TiO_2$. The use of a bubble column in which the catalyst is suspended in a liquid phase produces at least the productivity of a fixed bed reactor, and the selectivity of a perfectly stirred reactor.

DESCRIPTION OF THE INVENTION

The present invention concerns a process for synthesising hydrocarbons from a mixture comprising carbon monoxide and hydrogen, CO—$H_2$, optionally carbon dioxide $CO_2$, in the presence of a catalyst essentially constituted by a metal alloy comprising at least one metal selected from metals from groups 8, 9 and 10, preferably iron or cobalt, used in suspension in a liquid phase in a reactor which is usually operated in the presence of three phases: a liquid phase, a gas phase and a solid phase which is at least partially constituted by the catalyst (slurry reactor).

The catalyst used in the process of the invention is essentially constituted by a metal alloy containing at least about 60% by weight of a metal selected from metals from groups 8, 9 and 10, preferably at least 70% by weight of at least one metal selected from metals from groups 8, 9 and 10, more preferably at least 80% of at least one metal selected from metals from groups 8, 9 and 10.

The grain size of the catalyst is generally less than about 700 microns, preferably less than about 250 microns, more preferably in the range 1 to 150 microns, very preferably in the range 10 to 80 microns, for optimum use of a reactor operating in the liquid phase, in particular a slurry bubble column type three phase reactor.

The catalyst used in the process of the invention can be prepared using any technique which is known to the skilled person to prepare Raney alloys. In particular, it can be prepared using the methods described in U.S. Pat. Nos. 1,628,190, 1,915,473, 2,977,327 and EP-A-0 648 534. Those methods can optionally be modified by the skilled person to obtain the desired characteristics.

One preferred method for preparing this catalyst consists in forming an alloy between the two metals, for example cobalt and aluminium, at high temperature (1300° C.), forming by spraying, then activating with a sodium hydroxide solution to produce the catalyst which is ready for use after separating the sodium aluminate solution.

The catalyst can optionally contain at least one additional element selected from alkali metals or metals from groups 4, 5, 6, 7, 8, 9, 10 or 11 of the new periodic table. This additional element is preferably selected from the group formed by titanium, zirconium, iron, ruthenium, molybdenum, tungsten and tantalum.

The weight content of an additional element with respect to the total catalyst weight is preferably in the range 0 to about 12% by weight, more preferably in the range 0.01% to 10% by. weight, very preferably in the range 0.1% to 5% by weight. These additional elements can be introduced at the same time as the metal or metals selected from elements from groups 8, 9 or 10, or during at least one subsequent step.

The present invention concerns a process for converting synthesis gas using a catalyst with particular stable performances, leading to a mixture of essentially linear and saturated hydrocarbons generally containing at least 50% by weight of $C_5^+$ hydrocarbons and generally less than 20% by weight of methane, preferably less than 15% by weight of methane with respect to the total amount of hydrocarbons formed.

This process is carried out at a total pressure which is normally in the range 0.1 to 15 MPa, radical in the range 1 to 10 MPa, and at a temperature generally in the range 150° C. to 350° C., preferably in the range 170° C. to 300° C. The hourly space velocity is normally in the range 100 to 2000 volumes of synthesis gas per volume of catalyst per hour, preferably in the range 400 to 5000 volumes of synthesis gas per volume of catalyst per hour. The $H_2/CO$ mole ratio of the synthesis gas is normally in the range 1:2 to 5:1, preferably in the range 1.2:1 to 2.5:1.

The conditions for using said catalysts in the process of the invention are generally as follows:

The catalyst is generally used directly in the reaction, without prior treatment, and in the form of a fine calibrated powder (grain size generally less than about 700 microns) in the presence of a liquid phase. The liquid phase can be constituted by at least one hydrocarbon containing at least 5 carbon atoms per molecule, preferably at least 10 carbon atoms per molecule. Preferably, this liquid phase is essentially constituted by paraffins, more preferably paraffins from a Fischer-Tropsch process. In general, the cut selected has an initial boiling point and an end point such that it is in the kerosene or gas oil range.

It can also be modified by pre-treatment before introduction into the reactor. This pre-treatment can, for example be:

washing to remove traces of the activation solution;

reduction carried out in the gas phase or in the liquid phase at a temperature in the range 100° C. to 600° C., preferably in the range 150° C. to 400° C., at a pressure in the range 0.1 to 10 MPa and at an hourly space velocity in the range 100 to 40000 volumes of mixture per volume of catalyst per hour, preferably in the range 500 to 10000 volumes of mixture per volume of catalyst per hour.

When this reduction is carried out in the liquid phase, the catalyst is suspended in an inert solvent, for example a paraffinic cut comprising at least one hydrocarbon containing at least 5 carbon atoms per molecule, preferably at least 10 carbon atoms per molecule.

The catalyst is advantageously used in a slurry bubble column type slurry reactor. This type of implementation has the advantage over other types, such as a fixed bed, of resulting in:

optimum use of the catalyst performances (activity and selectivity) by limiting intra-granular diffusion phenomena, substantial limitation of thermal effects in the catalyst grain, which is surrounded by liquid.

This type of implementation requires that the catalyst and reaction products be separated. Separation can be carried out in the reactor or outside the reactor.

In the first case, filtering elements are interposed in the line for evacuating the products from the reactor, and maintaining all of the catalyst in the reactor, as described in European patent application EP-A-0 609 079.

In the second case, the suspension (slurry) is generally circulated using a pump, for example. A variety of separation means can be used, as indicated in International patent application WO-A-97/31693.

These two separation modes can be employed when using the catalyst in the process of the invention, but it has generally been observed that this catalyst can readily be separated from the reaction products using techniques which are known to the skilled person, such as filtration, centrifugal separation, decanting, magnetic separation or hydrocyclone separation.

Further, one advantage of the catalyst used in the process of the invention is that its high metal content leads to a relatively high density and to ready separation of the great majority of the catalyst using, simple decanting, for example. More generally, the catalyst used has a bulk density of more than 1.2 kilograms per litre (kg,/l), preferably more than 1.5 kg/l, more preferably more than 1.8 kg/l.

In summary, the invention concerns a process for synthesizing hydrocarbons from synthesis gas, in the presence of a catalyst essentially constituted by a Raney metal alloy dispersed in a liquid phase, in which the catalyst comprises at least 60% by weight of at least one metal selected from metals from groups 8, 9 and 10. Preferably, said metal is selected from iron and cobalt.

The catalyst of the process of the invention can also comprise at least one additional element selected from alkali metals and metals from groups 4, 5, 6, 7, 8, 9, 10 and 11. Preferably, this additional element is selected from the group formed by titanium, zirconium, iron, ruthenium, molybdenum, tungsten and tantalum. The weight content of the additional element with respect to the total catalyst weight is in the range 0 to about 12% by weight, preferably in the range 0.01% to 10% by weight, more preferably in the range about 1% to 5% by weight. In general, the grain size of the catalyst is less than about 700 microns.

Preferably, the liquid phase used in the process of the invention is a kerosene cut or a gas oil cut from the Fischer-Tropsch process.

The catalyst can optionally be modified by means of a pre-treatment before introduction into the reactor, for example by reduction carried out at a temperature in the range 100° C. to 600° C., a pressure in the range 0.1 to 10 MPa and at an hourly space velocity in the range 100 to 40000 volumes of mixture per volume of catalyst per hour.

Preferably, the catalyst is used in a reactor operating in the liquid phase, such as a slurry bubble column.

The following examples illustrate the invention.

EXAMPLE 1 (IN ACCORDANCE WITH THE INVENTION)

Catalyst A

A catalyst A of the Raney cobalt type sold by Degussa with reference B2112Z was in the form of a powder, pre-activated and stored under water, in the absence of air. The grain size of the metal powder was in the range 1 to 130 microns.

The cobalt metal content in catalyst A was more than about 95% by weight.

EXAMPLE 2 (IN ACCORDANCE WITH THE INVENTION)

Catalyst B

A catalyst B of the Raney cobalt type sold by Degussa with reference Cobalt beta-1000 was in the form of 4 millimetre by 4 millimetre pellets.

Wet grinding of these pellets, which were stored under water, was carried out to reduce the grain size of the catalyst and keep it in the absence of air. The grain size of the recovered powder was in the range 1 to 130 microns.

The cobalt metal content in catalyst B was about 60% by weight.

EXAMPLE 3 (COMPARATIVE)

Catalyst C

A catalyst C with formula $Co/Al_2O_3$ was prepared by impregnating an alumina powder with a specific surface area of 180 m²/g. This support was in the form of a powder with a grain size in the range 10 to 150 microns.

After impregnation, the support was dried and calcined at 400° C.

The final cobalt content was 12.5%.

EXAMPLE 4
Catalytic Tests

Catalysts A, B and C described in Examples 1 and 2 above were tested in a reactor operating in the liquid phase with a catalyst in suspension (slurry). The reactor was perfectly stirred, functioned continuously and operated with a concentration of 10% by volume of catalyst in the suspension.

The test conditions were as follows:

temperature 230° C.;

pressure =2 MPa;

hourly space velocity (HSV)=1000 h$^{-1}$

H$_2$/CO mole ratio=2/1

TABLE 1

Conversion of synthesis gas to hydrocarbons

| Catalyst | CO conversion (vol % after 100 h) | Distribution of products formed (weight %) | | |
|---|---|---|---|---|
| | | C1 | C1–C4 | C5+ |
| A (invention) | 56 | 9 | 25 | 66 |
| B (invention) | 46 | 8 | 23 | 69 |
| C comparative) | 45 | 12 | 27 | 61 |

The results show that catalysts A and B of the invention led to a more substantial formation of C5 +hydrocarbons than comparative catalyst C.

EXAMPLE 5
Catalytic Tests in Bubble Column

The catalysts described in Examples 1 and 2 were used in a slurry bubble column with an internal diameter of 50 mm and a height of 1500 mm. This column was also equipped with a synthesis gas inlet manifold at the bottom of the column, with a suspension extraction pipe above the liquid level, with a suspension re-injection pipe at the column bottom, and with a circulating loop comprising a degasser, a decanter and a pump.

500 g of catalyst A in 1.5 1 of n-C18 paraffin was introduced into the column and used under the following conditions:

Feed flow rate: 1 m³/h of CO+H$_2$ mixture,

H$_2$/CO mole ratio: 1/2;

Temperature: 220° C., and total pressure: 20 bars.

The CO conversion was 72% and the selectivity for C5 +hydrocarbons was 78%. The catalyst was separated from the liquid products using a decanter; the amount of catalyst in the liquid after decanting was less than 100 ppm by weight.

Catalyst C was used under the same conditions as catalyst A. It led to a CO conversion of 61%, and to a C5+hydrocarbon selectivity of 72%. After decanting in the same apparatus, the liquid obtained contained 0.15% by weight of catalyst, which meant that filtering had to be carried out after decanting.

These examples show the importance of the catalyst used in the process of the invention when using the slurry implementation. The catalyst used in the process of the invention produced more C5+hydrocarbons. It was easier to separate from the liquid products using a simple technique such as decanting, for example.

What is claimed is:

1. A process for synthesizing hydrocarbons from synthesis gas comprising carbon monoxide, said process comprising contacting said synthesis gas under hydrocarbon synthesis conditions with a catalyst comprising a Raney metal alloy dispersed in a liquid phase, in which the catalyst comprises 60% by weight of cobalt.

2. A process according to claim 1, said catalyst further comprising at least one additional element selected from alkali metals and metals from groups 4,5,6,7,8,9, 10 and 11.

3. A process according to claim 2, in which the additional element is selected from the group formed by titanium, zirconium, iron, ruthenium, molybdenum, tungsten and tantalum.

4. A process according to claim 3, in which the amount of additional element with respect to the total weight of catalyst is in the range of from above 0 to about 12% by weight.

5. A process according to claim 1, in which the grain size of the catalyst is less than about 700 microns.

6. A process according to claim 1, in which the liquid phase is a kerosene or gas oil cut from the Fischer-Tropsch synthesis.

7. A process according to claim 1, in which the catalyst is modified by means of a pre-treatment before introducing it into the reactor.

8. A process according to claim 7, in which the pre-treatment is a reduction carried out at a temperature in the range 100° C. to 600° C., at a pressure in the range 0.1 to 10 MPa and at an hourly space velocity in the range 100 to 40000 volumes of mixture per volume of catalyst per hour.

9. A process according to claim 1, in which the catalyst is used in a slurry bubble column reactor.

10. A process according to claim 3, in which the amount of additional element with respect to the total weight of catalyst is in the range of from above 0 to about 12% by weight.

11. A process according to claim 10, in which the grain size of the catalyst is less than about 700 microns.

12. A process according to claim 11, in which the catalyst is used in a slurry bubble column reactor.

\* \* \* \* \*

UNITED STATES PATENT AND TRADEMARK OFFICE
CERTIFICATE OF CORRECTION

PATENT NO. : 6,391,929 B1
DATED : May 21, 2002
INVENTOR(S) : Hughes et al.

It is certified that error appears in the above-identified patent and that said Letters Patent is hereby corrected as shown below:

<u>Title page,</u>
Item [54], delete "DISPERDED" and insert -- DISPERSED --.

Signed and Sealed this

Eighteenth Day of February, 2003

JAMES E. ROGAN
*Director of the United States Patent and Trademark Office*